United States Patent [19]

Miodownik

[11] 4,450,838

[45] May 29, 1984

[54] JET VENTILATOR CONTROL SYSTEM

[75] Inventor: Saul Miodownik, New York, N.Y.

[73] Assignee: Memorial Hospital for Cancer and Allied Diseases, New York, N.Y.

[21] Appl. No.: 233,244

[22] Filed: Feb. 10, 1981

[51] Int. Cl.³ .............................................. A61M 16/00
[52] U.S. Cl. ................................ 128/204.23; 128/696
[58] Field of Search ...................... 128/204.21, 204.23, 128/716, 696, 702–708

[56] References Cited

U.S. PATENT DOCUMENTS 4,155,356  5/1979  Venegas ........................... 128/204.23
4,215,681  8/1980  Zalkin et al. ..................... 128/204.21

FOREIGN PATENT DOCUMENTS 2736541  2/1979  Fed. Rep. of Germany ...... 128/706
552969   4/1975  U.S.S.R. ........................... 128/204.21

OTHER PUBLICATIONS

Engelman, F. A. et al., "Digital Electronic Control of Automatic Ventilators", IEEE BME Trans., vol. 24, #2, Mar. 1977, pp. 188–190.
Woo, J. et al., "Analysis & Simulation of an Adoptive System for Forced Ventilation of the Lungs", IEEE BME Trans., vol. BME-22, No. 5, Sep. 1975.
Marsh, W. I. et al., "A Flexible System for Closed Loop Ventilator Development", Proc. 14th Hawaii Intnl. Conf. on System Sciences, pp. 457–462, (1981).
Cook & Webster's *Therapeutic Medical Devices*, Ch. 13, Prentice-Hall, 1982.

*Primary Examiner*—Kyle L. Howell
*Assistant Examiner*—Francis J. Jaworski
*Attorney, Agent, or Firm*—Felfe & Lynch

[57] ABSTRACT

A jet ventilator control system produces a periodic pulse signal either asynchronous or synchronous with a patient's pulse rate. It is proportional in frequency to the number of jet ventilation pulses to be applied to the patient per unit time and is digitally programmable to adjust the delay and duty cycle of the pulse signal within the period defined by the produced pulse. The duration and duty cycle adjusted pulse signals effect the application of jet ventilation pulses corresponding thereto to the patient.

10 Claims, 16 Drawing Figures

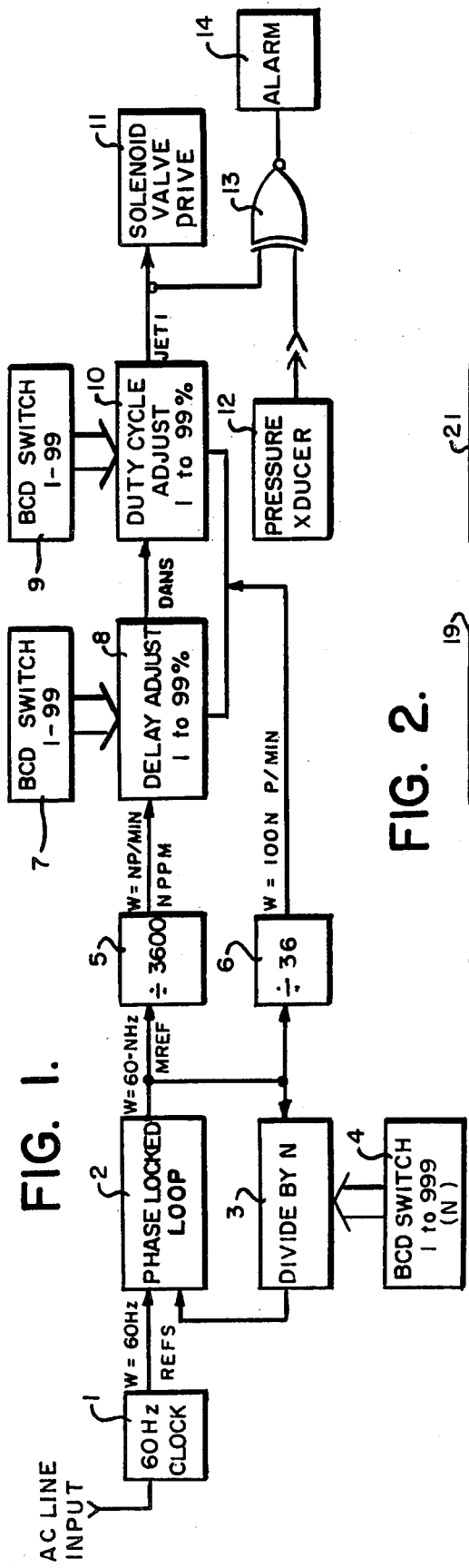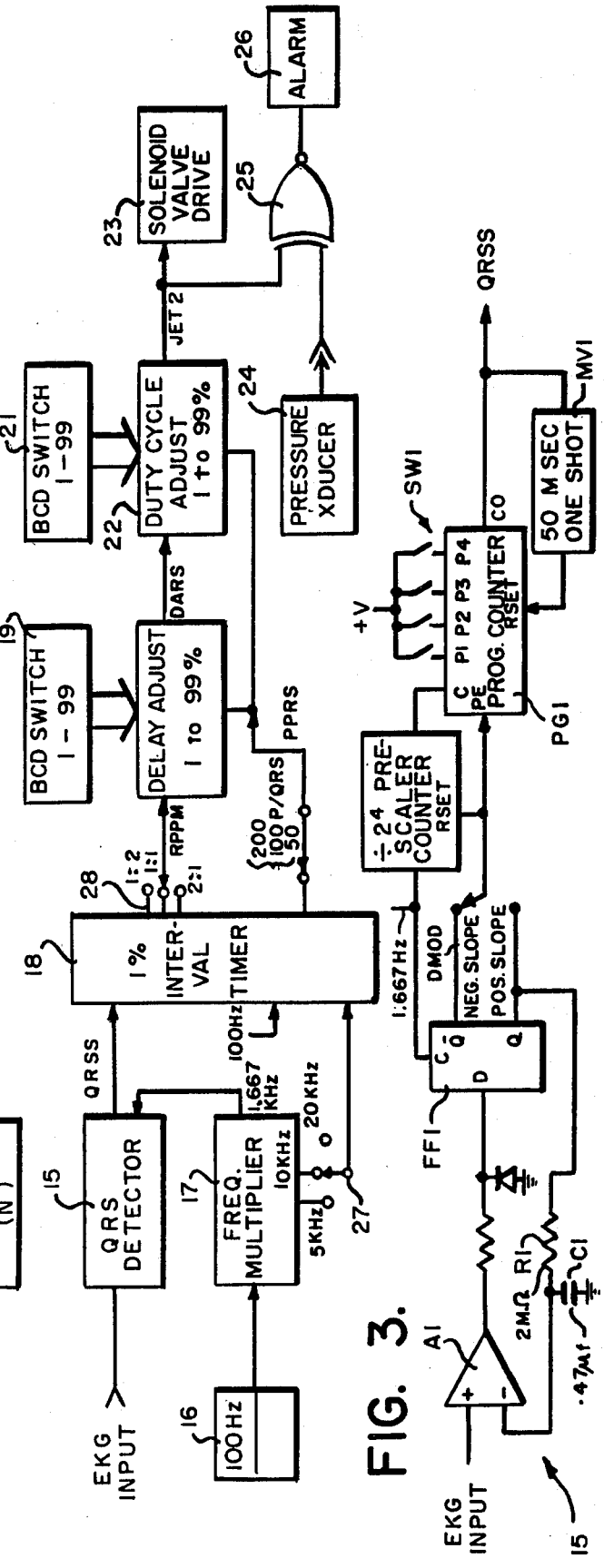

SIGNAL FLOW PATH OF JET VENTILATOR CONTROLLER IN CARDIAC SYNCHRONIZED MODE WITH PROPOGATION DELAY COMPENSATION

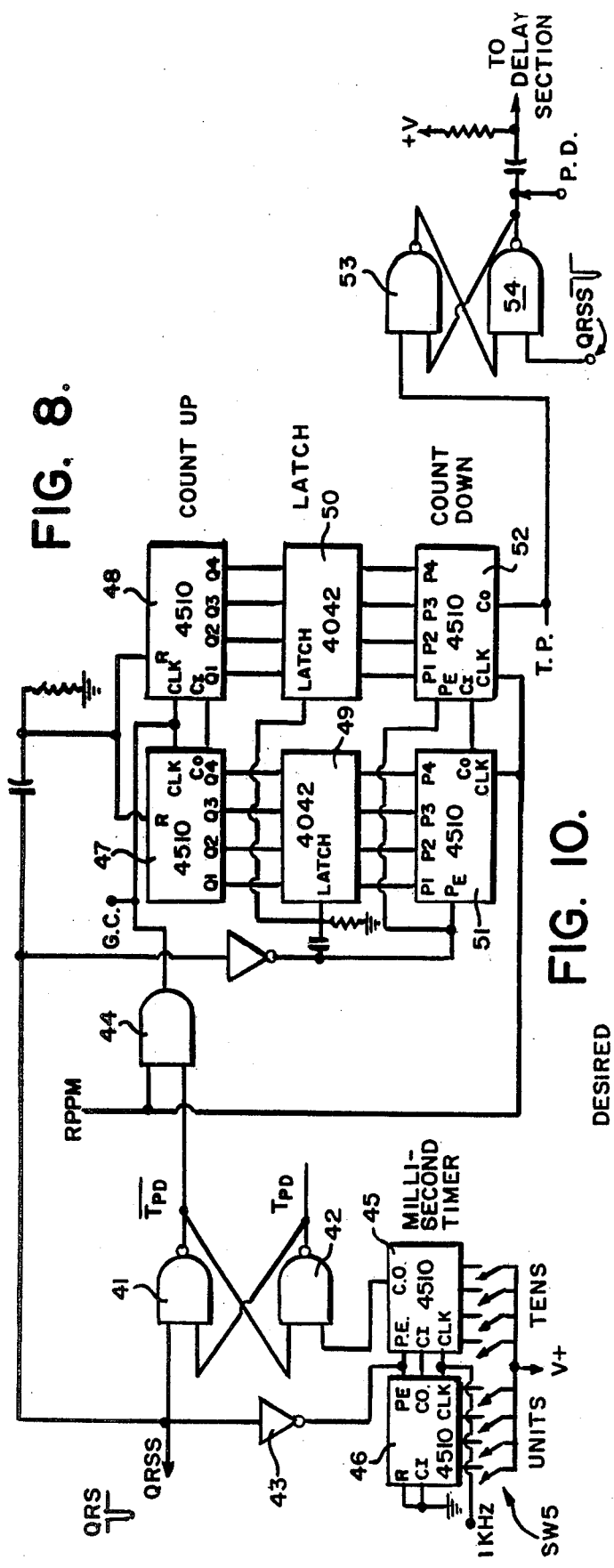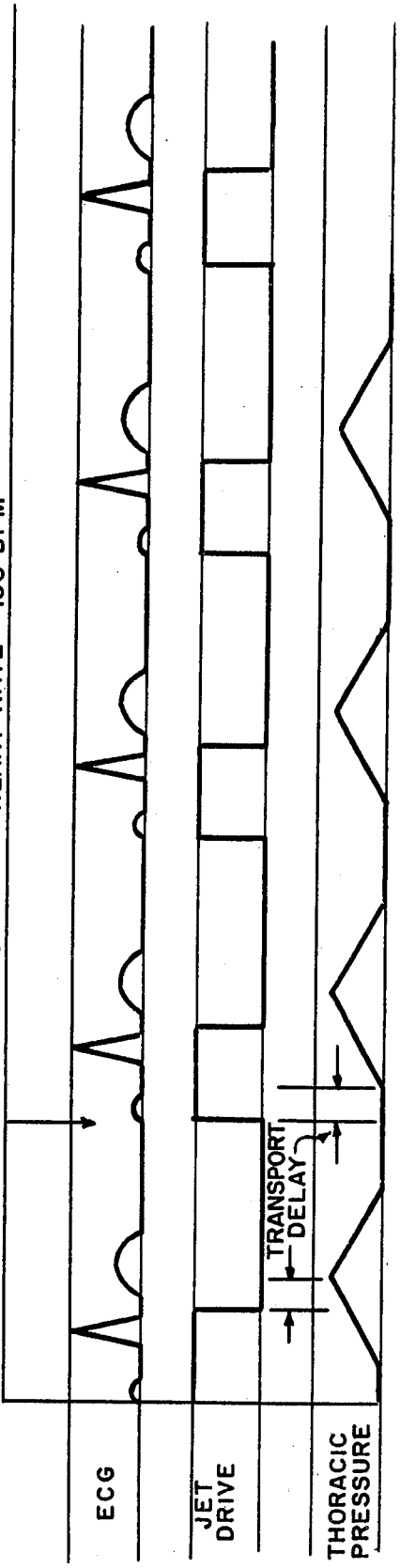

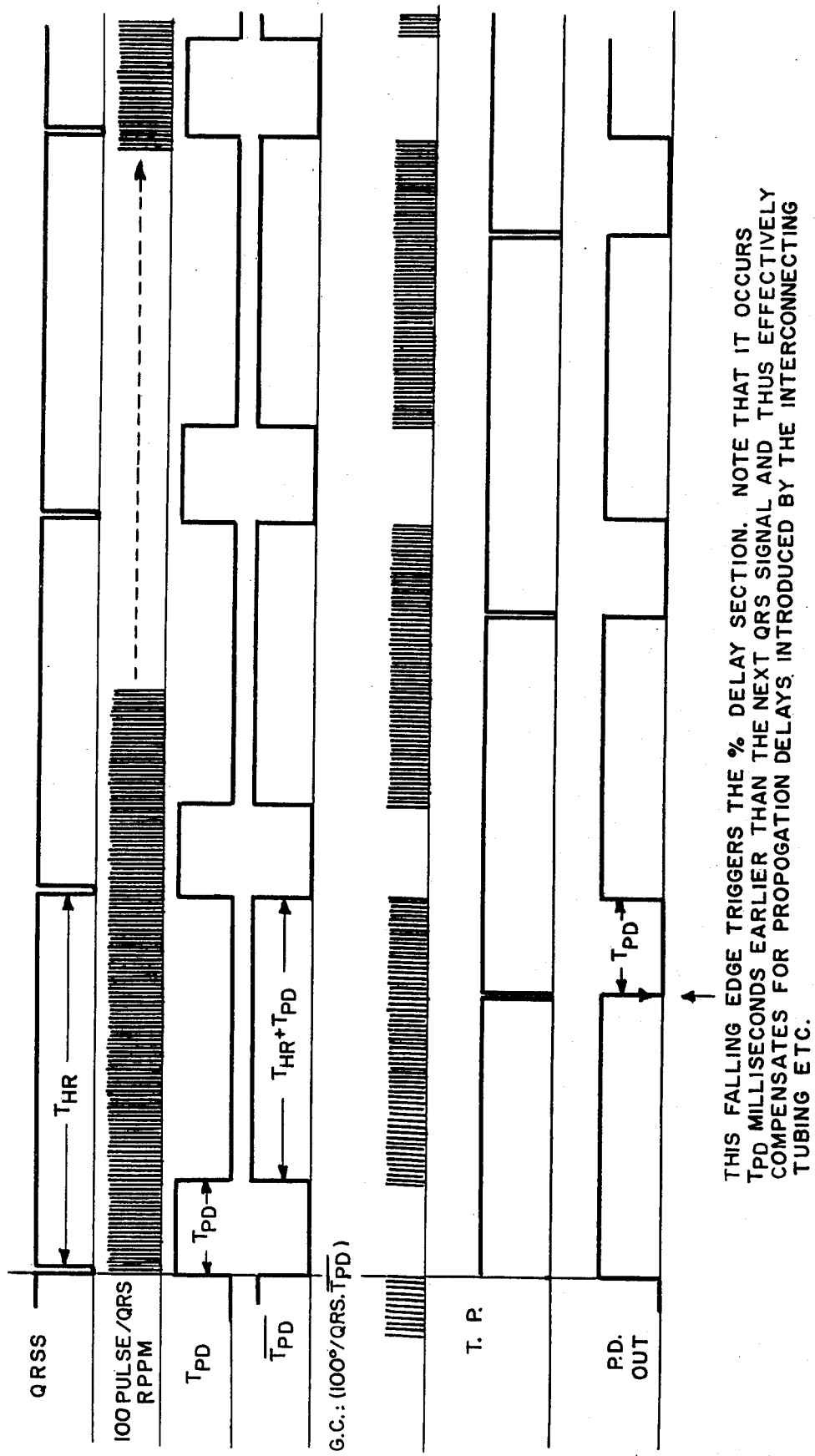

JET VENTILATOR CONTROL SYSTEM

BACKGROUND OF THE INVENTION

The present invention relates to a control system for a jet ventilator.

Jet ventilators, and in particular high frequency jet ventilators, operate by introducing into the airway of a patient a relatively small volume of gas on the order of 100 milliliters at a high velocity by way of a short pulse of, for example, 130 milliseconds. This high speed stream will entrain and accelerate a larger volume of stationary gas through the airway. The pulse duty cycle of typically 33 percent on and 66 percent off is repeated up to several hundred times per minute, resulting in adequate ventilation to the patient's lungs.

In conventional high speed jet ventilators, the control therefore is asynchronous with respect to the cardiac rate of the patient and moreover is merely coarsely adjustable with respect to the duty cycle of the ventilation pulse.

SUMMARY OF THE INVENTION

The main object of the present invention is to provide a high speed jet ventilator control system which is capable of being digitally programmed for both asynchronous and cardiac synchronized modes.

These and other objects of the present invention are carried out by a digitally programmable high frequency jet ventilator control system which is capable of cardiac synchronization and controls a high flow/high speed solenoid valve with a digital timing network that permits precise selection of respiratory rate, inspiratory to expiratory ratio and percent delay based on the patient's EKG when the synchronized mode is utilized. The gas is delivered to the patient via a high-speed, pressure-blended oxygen-air source, the aforementioned solenoid valve and control system, a short length of low compliance connecting tubing and a small diameter injector that is placed strategically in the patient's airway.

While the control system according to the present invention has been utilized to drive an Automatic Switch Company solenoid valve no. 8262B2080N, the valve is independent of the control system and a wide variety of valves may be driven both in the asynchronous and synchronous mode by the control system according to the present invention.

The system according to the present invention is capable of operating in the asynchronous mode alone, the synchronous mode alone or may switch from the synchronous to the asynchronous mode upon the failure to detect an EKG pulse from the patient. In the asynchronous mode, the timing signals that determine respiratory rate and duty cycle (inspiratory/expiratory ratio) are derived from a stable reference frequency source. In a preferred embodiment of the present invention, this stable reference frequency source is the 60 Hz power line frequency, however, one skilled in the art would recognize that a crystal controlled frequency reference may be alternatively used. A phase locked loop, a programmable digital frequency divider and associated divider chains are used to generate respiratory rates from 1 through 999 breaths or ventilations per minute. At the same time, each respiratory cycle is divided into 100 parts. By counting a selectable number of these pulses during each respiratory cycle, any desired duty cycle from 1 through 99 can be readily achieved. The signal that is thus generated is applied to a solenoid driver circuit which gates the gas supply to the patient. A pressure transducer is connected to the gated gas line near the patient's airway cannula to sense the pressure pulse generated by the gating action of the solenoid. This signal is constantly compared to the solenoid drive signal and forms the basis for an alarm system that will alert the staff to a variety of ventilator and gas supply failures. The alarm circuit looks for an approximate coincidence between the solenoid drive pulse and the pressure level derived from the patient's airway cannula. Should the gas source fail, the solenoid lock in the open or closed position, the line to the patient kink, or the pressure signal and the drive signal fall out of coincidence, the alarm will sound. This circuit is in effect for both the synchronous and asynchronous modes.

In the EKG synchronized mode, a much greater range of timing signals must be synthesized in order to effectively carry out the synchronization. The same 60 Hz power line reference can be used to generate these signals. Further, a very accurate QRS detector which detects the QRS wave coming from the output of the EKG is utilized to extract the pulse rate from the patient's EKG signal. The EKG signal should be between 0.25 and 2.5 volts and is available from any conventional patient cardiac monitor. Since it is impossible to predict the timing between successive QRS waves, the circuit digitally determines the previous pulse interval and generates the proper signals to activate the solenoid. Since the patient's heart rate may vary widely, the control system has the ability to set the respiratory rate at one-half, one or two times the heart rate, as desired. As in the asynchronous mode, 100 pulses are generated for each breath in the one percent interval timer according to the present invention. These are counted by two digital circuits, the first determining the time delay between the onset of the pulse signal and the gating of the solenoid valve and the second circuit determining the duty cycle of each breath. Both of these values are represented as a percentage of the previous pulse interval and continuously track the patient's changing heart rate. By adjusting the percent delay, it is possible to position the airway pressure pulse during any portion of the cardiac cycle. Doing so may enhance the cardiac output by a variety of mechanisms that effect either the right or left side of the heart. To visualize this, a cursor is generated from the airway cannula pressure transducer and is placed on an oscilliscopic display of the patient's systemic or pulmonary artery pressure signal. This allows positioning the jet pressure pulse with an accuracy of plus or minus one percent of the previous pulse interval. In the synchronous mode, respiratory rates will track heart rates from a lower limit of 25 beats per minute to an upper limit of over 750 beats per minute. Duty cycle, as in the asynchronous mode, can be selectable from 1 to 99 percent.

It has also been found that, when using the jet ventilator in the cardiac synchronization mode, there exists a measurable, constant time delay from the QRS wave (opening of a cardiac valve) to the appearance of the pressure pulse which may enhance cardiac output within the thoracic cavity. Although delay control section positions the jet signal anywhere in the cardiac cycle, this timing relationship is only valid for the generation of the electronic signals themselves. The physical properties of the solenoid valve, the interconnecting tubing, and the patient's anatomy introduce additional fixed delays that must be reckoned with. Additionally, since these delays are assumed to be constant and the patient's heart rate will very likely vary over a course of treatment, these delays will cause temporal positioning errors of the jet pressure pulse with respect to the desired portion of the cardiac cycle. This problem is overcome according to the present invention by the provision of digitally programmable circuitry which compensates for the propagation delay by digitally programmably selecting a propagation delay for the jet pulse prior to its application to the solenoid valve.

Other advantages of the present invention will become more apparent from the detailed description of the invention with reference to the attached drawings wherein:

BRIEF DESCRIPTION OF THE DRAWINGS

FIG. 1 is a block diagram of the asynchronous control system according to the present invention;

FIG. 2 is a block diagram of the synchronous control system according to the present invention;

FIG. 3 is a schematic of the QRS detector according to the present invention;

FIG. 8 is a detailed schematic of the propagation delay means of FIG. 7;

FIG. 9 is a timing chart of the signals of FIG. 8;

FIG. 10 is graph of the actual transport delay.

DETAILED DESCRIPTION OF THE INVENTION

Figures 4, 7:
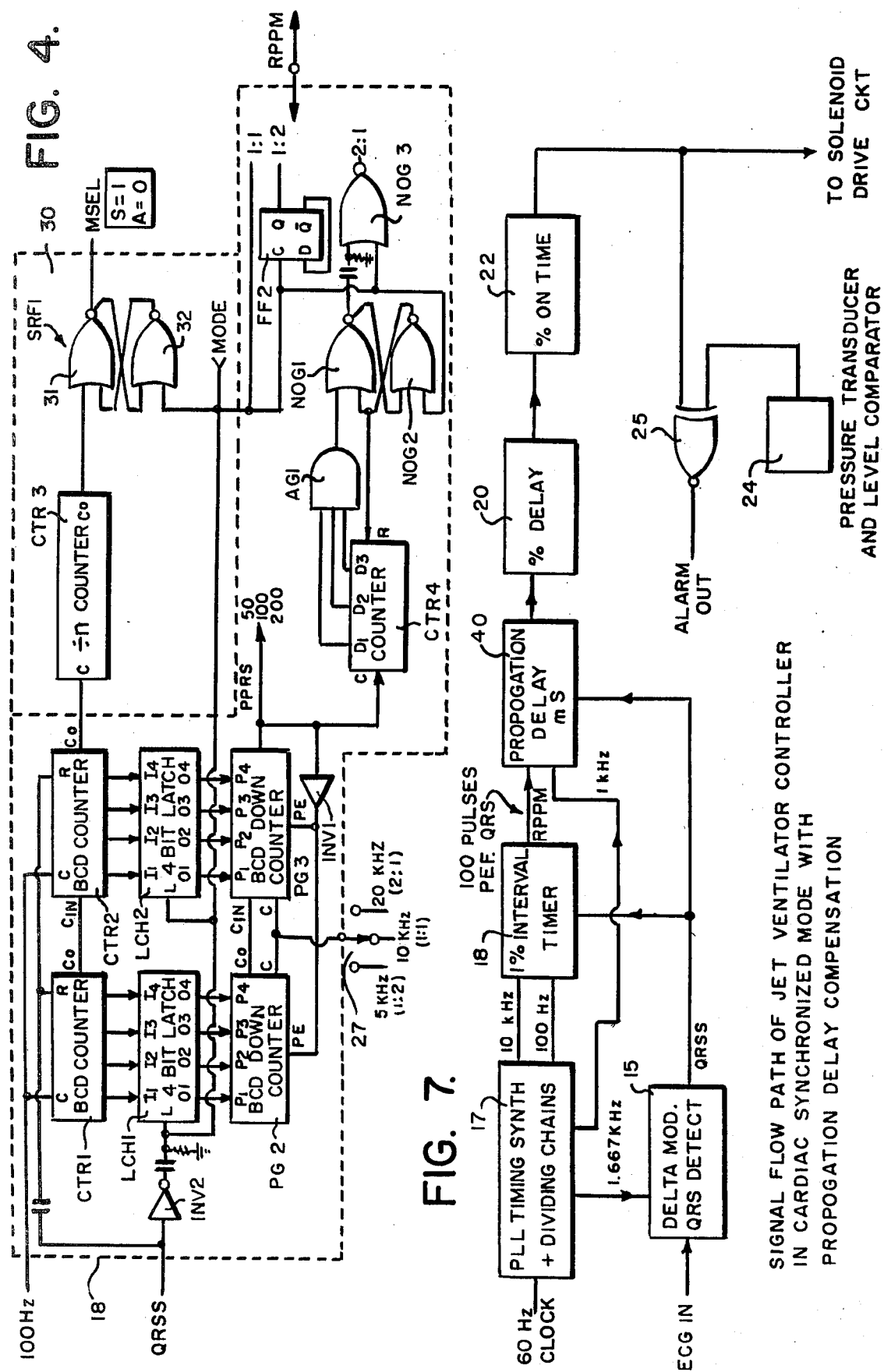
FIG. 4 is a schematic of the interval timer of the synchronous mode control system according to the present invention.
FIG. 7 is schematic diagram of a modification of the synchroneous system according to the present invention.

Referring now to FIG. 1, the asynchronous jet ventilator control system is shown in block diagram form.

The AC line input is fed to circuit 1 which generates a digital logic clock signal REFS of 60 Hz therefrom. While the circuitry is shown utilizing the 60 Hz clock generated from the AC line input, it is well understood by those skilled in the art that a crystal oscillator input or equivalent thereof can be utilized to generate the clock signal. The 60 Hz reference signal REFS is fed into a frequency multiplier which multiplies the 60 Hz signal by N to form signal MREF. This frequency multiplier includes phase locked loop 2 which has a divide by N programmable counter 3 in the feedback loop thereof. The multiplying factor N is determined by a BCD switch 4 which includes three decades and which pre-sets the counter 3 to the desired number N. Thereafter, the multiplied signal MREF is divided by 3600 in counter 5 to obtain signal NPPM which, in effect, has a frequency of N pulses per minute. Thus, the BCD switch bank 4 enables the user to digitally program the controller to set the asynchronous pulse rate thereof from 1 to 999 pulses per minute. In this manner, the pulse rate of the patient can first be checked by manual means and the control system can be set via switch 4 to approximate the pulse rate of the patient during use.

The programmed asynchronous pulse rate signal NPPM is then fed to a delay section 8 which is digitally programmable via BCD switch 7 which has two decades and thus a count from 1 to 99 to achieve a delay of from 1 to 99 percent of the pulse cycle. This is achieved by utilizing a pulse signal having the frequency of 100 N pulses per minute which is obtained by taking the output of the phase locked loop 2 and dividing it by 36 in counter 6. The delay adjusted signal DANS is then fed to the duty cycle adjust section 10 which is also digitally programmable via BCD switch 9 which has two decades of switches capable of selecting a number from 1 to 99. The duty cycle adjust section is capable of adjusting the duty cycle from 1 to 99 percent of the pulse width by utilizing the 100 N pulse per minute signal from divider 6. The output of the duty cycle adjust section 10, JET 1, is then directed to the solenoid valve drive 11 which controls the supply of pressurized air to the patient. The JET 1 pulse also is fed to an exclusive NOR gate 13 which receives at its other input the processed output of a pressure transducer 12 which is situated in the airway cannula and which, in the normal mode of operation, produces a pulse train which is slightly delayed from the JET 1 pulse. Thus the exclusive NOR gate will always produce a zero going signal during normal operation such that the alarm 14 is not actuated. If for some reason the JET 1 pulse disappears due to a malfunction or the pressure transducer 12 does not sense a pulse in the airway, the alarm 14 will go off.

Figure 5:
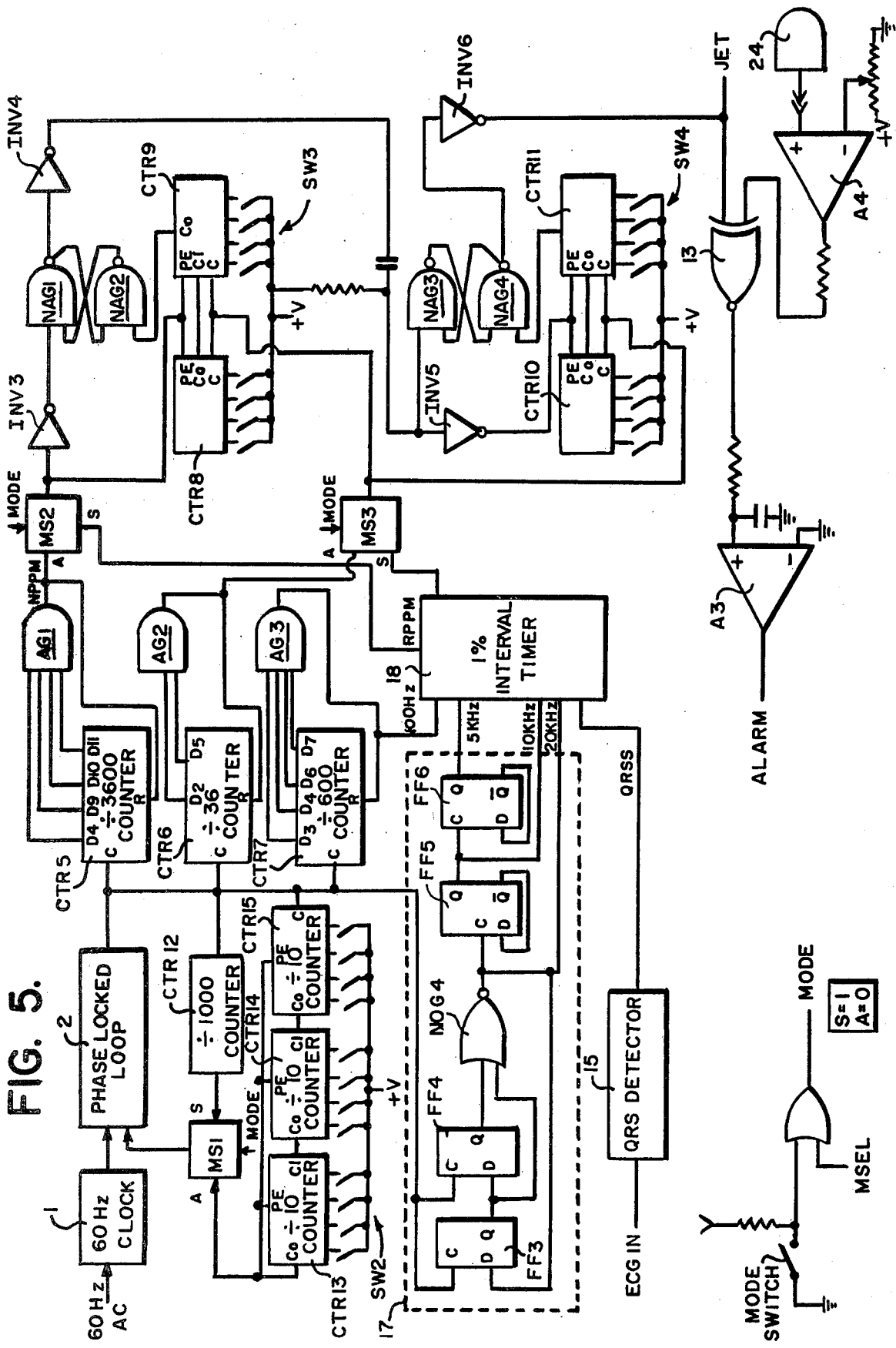
FIG. 5 is a schematic of the combined synchronous and asynchronous system according to the present invention.

Referring now to FIG. 2, the embodiment of the present invention for carrying out the EKG synchronous mode is shown. It should be noted, however, that the separate system for the synchronous mode is shown herein solely for the purposes of illustration and that, in the preferred embodiment of the present invention, the structural elements for both the asynchronous and synchronous mode are combined as shown in FIG. 5 wherein duplicated elements are eliminated in the interests of simplicity and economy.

As shown in FIG. 2, the EKG input from the monitor is fed to a QRS detector 15 which forms a digital output signal synchronized to the pulse rate (EKG QRS wave) of the patient.

A particularly advantageous embodiment of a QRS detector is shown in FIG. 3 which locks onto the R wave of the EKG input and such will be explained in detail hereinafter.

In order to obtain the delay and duty cycle adjustment from 1 to 99 percent in the synchronous mode as in the asynchronous mode, it is necessary to divide the period of the QRS detected signal QRSS into 100 parts as in the asynchronous mode. This is carried out by the one percent interval timer 18 which utilizes various high speed input signals of 5 kilohertz, 10 kilohertz, and 20 kilohertz frequency generated by a frequency multiplier 17 generated from a 100 Hz reference generator 16. The interval timer 18 also utilizes a 100 Hz signal and from these frequency input signals generates two output signals RPPM and PPRS. The signal RPPM constitutes the QRSS signal frequency multiplied by 50, 100 or 200 depending upon selecting of the 5 KHz, 10 KHz or 20 KHz signal selected by switch 27 at the input which in actuality selects the range depending upon the patient's pulse rate. In effect the respiratory rate can be set at one-half, one or two times the heart rate as desired where such is necessary in special instances. Also, depending upon the respiratory rate selected, the PPRS signal will either be 50, 100 or 200 pulses per QRSS signal thus enabling the delay adjust section 20 and the duty cycle adjust section 22 to set the desired delay and desired duty cycle as in the asynchronous mode. The desired delay and duty cycle adjustments are made via BCD switches 19 and 21 which enable the digital programming of delay and duty cycle adjustments by selecting a number from 1 to 99 in both corresponding to a delay of 1 to 99 percent of the period of RPPM and the duty cycle amounting to from 1 to 99 percent of the period of DARS. The output of the duty cycle adjustment section 22 is fed to the solenoid valve drive 23 and the alarm system which is equivalent to that of the asynchronous mode includes the pressure transducer 24, the exclusive OR gate 25 and the alarm 26, such as a buzzer or the like.

Referring now to FIG. 3, the QRS detector 15 is shown in more detail. The QRS detection is carried out by a delta modulator circuit which is intentionally designed to go into slope overload upon receipt of the R wave of the QRS signal. In normal operation, a delta modulator samples incoming analog data and outputs binary pulses whose polarity depends on the difference between the actual input signal and a quantized approximation of the preceding input signal. Thus the modulator's output reflects changes in the input and approximates the differential (delta) of the analog signal. In the circuit according to the present invention, an inherent limitation of the delta modulation circuit is taken advantage of by utilizing the overload condition thereof to indicate when a particular portion of a signal (the R wave) occurs within the entire EKG signal.

The delta modulator portion of the circuit 15 shown in FIG. 3 comprises the operational amplifier A1 whose positive input is connected to the EKG signal and whose output is fed through a resistor and cutoff diode to the input D of flipflop FF1. The clock input C receives a frequency signal from 1 to 5 KHz, preferably 1.67 KHz, in order to generate the delta modulation. The Q output of FF1 is fed back to the negative input of amplifier A1 through an RC network comprising resistor R1 and capacitor C1. It is in the RC network that the setting for the overloading of the delta modulator is required since this RC network determines the recovery time of the delta modulator. Since the R wave of the EKG signal has a higher rise time than the remaining P and T waves thereof, the values for C1 and R1 can be set so that the delta modulator will be in normal operation when the Q and S signals are received but will be thrown into an overload condition when the relative faster rise and fall time R wave is received. For a clock signal 1.67 KHz and an EKG input wherein the voltage thereof varies from 0.25 volts to 2½ volts, R1 equals 2 megohms and C1 equals 0.47 microfarads.

In order to digitally process the output of the delta modulator so as to distinguish between the overloaded condition of the delta modulator and the non-overloaded condition and therefore the difference between the received P and T waves and the received R wave, a scaling circuit is utilized to divide the 1.67 KHz clock signal down and the output thereof is fed to a programmable counter which has switches SW1 to enable same to count off a given amount of time. The output of the counter is fed back into the reset input thereof via a 50 millisecond one-shot multivibrator which has been added to prevent a double pulsing output when high amplitude and wide EKG complexes are input into the system.

The pre-set enable input of the programmable counter is alternatively connected to the positive or negative slope output of the delta modulator, and to the reset input of the pre-scaler counter. As a result, upon the receipt of each negative going pulse the counter is pre-set to a desired value corresponding to a gain of the system. If it is found that the delta modulator output for the P and T waves last no longer than five pulse widths, then the programmable counter is pre-set so that it initially loads a count of at least six. In this way, each time a pulse is received from the DMOD output of the delta modulator at the pre-set enable, the count of six is pre-set into the programmable counter. If the programmable counter is set into a count down mode, there will be no carry out signal therefrom unless the width of the DMOD output pulse is greater than six pulse-widths. Since this will only occur when an R signal is detected due to the overload condition of the delta modulator, there will only be a QRSS output signal for the detected R wave.

Figure 6A:
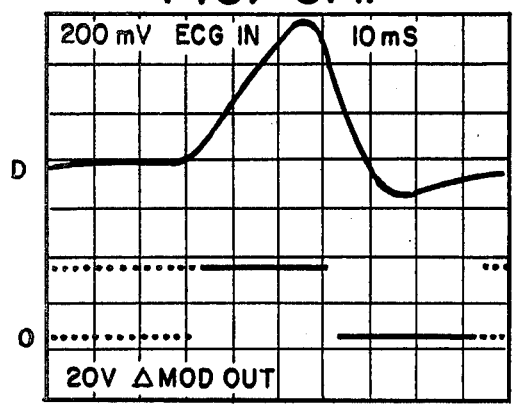
FIGS. 6a–6g are timing waveforms of the circuitry according to FIGS. 1–5.
Figure 6B:
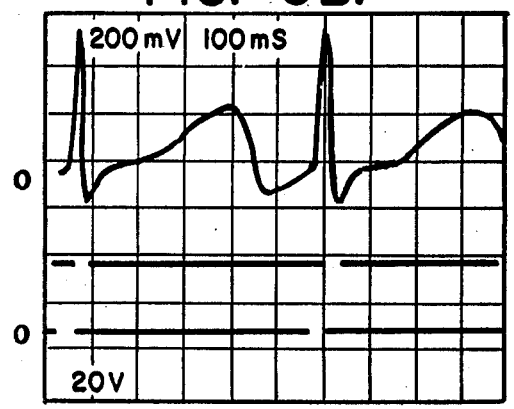

FIGS. 6A–6G show examples of the operation of the circuit of FIG. 3. In FIG. 6A, the top waveform illustrates an EKG input pulse and a lower signal shows the DMOD signal which is the output of the delta modulator. As can be seen therein, only during the R wave is there a wide pulse output from the delta modulator, since during the rising edge and the falling edge of the R wave the delta modulator is in overload. During the remaining portions thereof, the modulator is not in overload and thus the pulses are short. This can also be seen in FIG. 6B which shows two consecutive R waves at the top thereof and the pulse signals from the delta modulator output at the bottom thereof. The pre-scaler counter and programmable counter act to sense only the wide pulse width pulses thereby sensing the R wave.

Figure 6C:
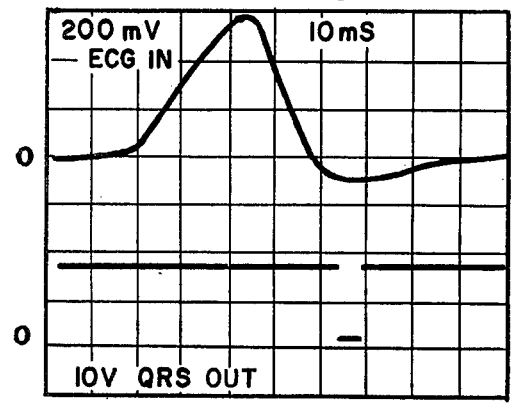

FIG. 6C shows at the top waveform the EKG input and at the bottom waveform the output QRSS from the QRS detector. As can be easily seen, the output from the programmable counter only occurs after the long pulse duration has been sensed. The distance of the QRSS pulse from the beginning of the pulse shown in FIG. 6A is determined by the pre-set count from switch SW1 for the programmable counter.

Figure 6D:
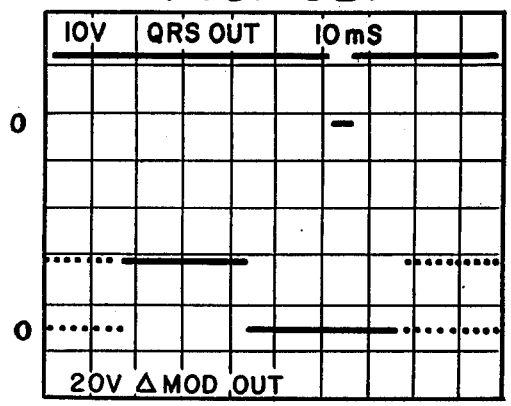

FIG. 6D shows this relationship between the DMOD output pulse and the QRSS output pulse as described.

Figure 6E:
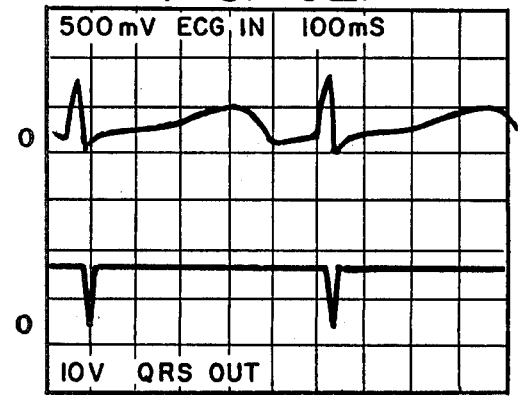

FIG. 6E shows two consecutive EKG signals with two consecutive QRSS output signals obtained by the QRS detector.

Figure 6F:
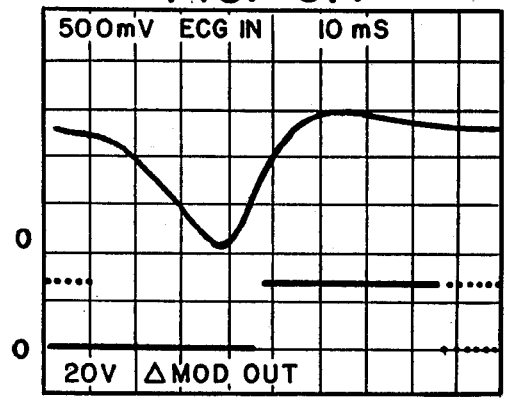
Figure 6G:
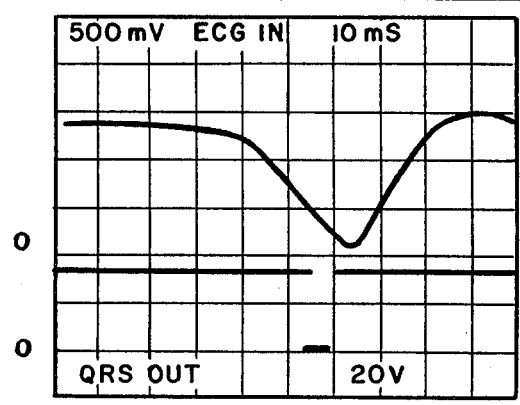

FIGS. 6F and 6G are similar to FIGS. 6A and 6C, except that a negative going ECG signal is illustrated.

FIG. 4 illustrates an embodiment of the one percent interval timer 18 described hereinabove with respect to FIG. 2.

As shown in FIG. 4, the interval timer 18 has the QRSS signal from the QRS detector 15 as an input to the reset terminals of four-stage binary counters CTR 1 and CTR 2 and to the latch input of four-bit latches LCH1 and LCH2 through an inverter INV2. The clock input for the BCD counters CTR1 and CTR2, which are connected in series as shown, is the 100 Hz signal. The interval timer also includes programmable binary down counters PG2 and PG3 which have the pre-set data inputs thereof connected to the outputs of the four-bit latches LCH1 and LCH2 and which are connected in series and have their pre-set enable connected through inverter INV1 to the carry out output of counter PG3 which corresponds to the signal PPRS. The clock input of the two programmable counters PG2 and PG3 is connected selectively to the 5 KHz, 10 KHz or 20 KHz output signal from the frequency multiplier 17 via switch 27.

In operation, the interval timer is initialized and after the first QRSS signal is received the BCD counters CTR1 and CTR2 begin counting at the 100 Hz rate. When the next QRS signal is received, the count in counter CTR1 and CTR2 is latched into latches LCH1 and LCH2 and the BCD counters CTR1 and CTR2 are reset. As a result, the period between the QRSS signals is broken down into a number of 100 Hz pulse increments, which are stored in the latched circuits LCH1 and LCH2. The BCD down counters PG2 and PG3 upon counting down to zero at the 10 KHz rate, for example, will load therein the data in latches LCH1 and LCH2 and count down therefrom again to zero at the 10 KHz rate. Each time the counters PG2 and PG3 count down to zero a PPRS pulse is produced and the data in the latches LCH1 and LCH2 are again loaded therein. Since the 10 KHz clock frequency is 100 times that of the 100 Hz clock frequency of the counters CTR1 and CTR2, 100 PPRS pulses will be produced between each QRSS pulse effectively dividing the period therebetween into one percent increments. If the 5 KHz rate is utilized, 50 PPRS pulses will be produced between consecutive QRSS pulses and if the 20 KHz frequency is utilized then 200 PPRS pulses will be produced between consecutive QRSS pulses.

The counter CTR4 receives the PPRS pulse at its clock input and the data outputs thereof are fed into AND gate AG1 whose output is inputted to set-reset flipflop SRF2 comprising NOR gates NOG1 and NOG2. The output of SRF2 is fed to NOR gate NOG3 and flipflop FF2 in order to create the RPPM signal described hereinbefore. The output, to wit, 1 to 1, 1 to 2, 2 to 1, is selected at the same time by switch 27 which selects either the 5 KHz, 10 KHz or 20 KHz clock signal.

Also shown in FIG. 4 is fail-safe circuitry 30 which is utilized to automatically switch the control system over from the synchronous to the asynchronous mode in the event that no EKG input is received from the patient. As shown, a divide-by n counter CTR3 receives the count output of series counters CTR1 and CTR2. The count n is selected as desired to indicate the time one desires to wait before switching over to the asynchronous mode. More specifically, the carry-out output of binary counter CTR2 occurs once every 2.56 seconds. Since the QRSS signal will re-set counters CTR1 and CTR2 before the one second point is reached, there is normally no output at the carry-out output of counter CTR2. If it is understood that if no QRSS output is obtained due to the fact that the ECG signal from the patient is flat due to a malfunction of the monitor or to the loss of pulse in the patient, it is even more desirable to continue the jet ventilation of the patient at this time rather than terminate the operation thereof. Thus, if the maximum desired time for failure to receive a QRSS signal is determined to be, for example, 10 seconds, then counter CTR3 is pre-set to count to the n=4. At this time, a carry-out output will be obtained and will set/reset flipflop SRF1 which comprises NOR gates 31 and 32. When the SFR1 flipflop is set by counter CTR3, the mode is automatically switched from the synchronous to the asynchronous mode. The signal MODE corresponding to the asynchronous mode also acts to disable the operation of latches LCH1 and LCH2 thereafter.

FIG. 5 shows the preferred embodiment of the present invention which is the combination of circuitry for carrying out either the asynchronous or synchronous mode of the jet ventilator control system.

Consistent with the circuitry shown in FIG. 1 for the asynchronous mode operation, a 60 Hz AC input is fed to a 60 Hz clock generator 1 to provide a reference signal for phase locked loop 2. A divide-by 3600 counter CTR5 provides the division function for the block 5 in FIG. 1, while the divide-by 36 counter CTR6 provides the division function for the divide-by 36 counter 6 shown in FIG. 1. Further, a divide-by 600 counter CTR7 is provided to obtain the 100 Hz signal when the unit is operating in the synchronous mode. This is possible, when in the synchronous mode, by means of a mode select switch MS1 which, receives the mode select control signal MODE and in the synchronous mode connects the divide-by 1000 counter CTR 12 into the feedback loop of the phase locked loop 2. Thus the output of the phase locked loop creates a 60,000 Hz clock signal which when divided by 600 yields a 100 Hz fixed reference signal. In the asynchronous mode, mode select switch MS1 connects the counters CTR13–15 into feedback loop of the phase locked loop 2, which are pre-set enabled counters therefore enabling the user to pre-set the desired multiplication factor for the frequency multiplier by digitally programming the decade BCD switches SW2 as described hereinbefore with respect to FIG. 1 and divide-by N counter 3 and BCD switch 4.

The counters CTR5–7 are enabled to count to their pre-determined counts by the use of AND gates AG-1–AG3 which feed back a re-set pulse when the desired count is reached.

Mode select switch MS2 determines whether the asynchronous signal NPPM from the output of AND gate AG1 or the synchronous signal RPPM from the output of the interval timer 18 is applied to the delay adjust circuitry depending upon, of course, whether the circuit is in the asynchronous or the synchronous mode.

The delay adjust section which was disclosed with respect to FIG. 1 including elements 7 and 8. FIG. 5 shows the specific circuitry for carrying out the delay adjustment and the duty cycle adjustment. The circuitry for carrying each out is substantially identical. The synchronous or asynchronous pulse (NPPM or RPPM) is received at inverter INV3 and fed to a set/reset flipflop comprising NAND gates NAG1 and NAG2, whose re-set input is received from the carry-out output of counter CTR9 which is connected in series with counter CTR8. The output of the gate NAG1 is then fed to inverter INV4 and constitutes the output (DANS or DARS) of the delay adjust section. Counters CTR8 and CTR9 which are pre-settable counters are connected to the decade switches SW3 which enable the pre-setting thereof upon the receipt of the output pulse from the mode select switch MS2. At the same time, the counters are clocked by the output of the mode select switch MS3 which provides the frequency multiplied (100 N) signal from the divide-by 36 counter CTR6 in the asynchronous mode or the output PPRS from the one percent interval timer 18 in the synchronous mode. The leading edge of the output pulse from mode select switch MS2 sets the flipflop comprising gates NAG1 and NAG2. Upon the counting of counters CTR8 and CTR9 from the pre-set amount corresponding to the percent of the period which is to be utilized as the delay, the set/re-set flipflop is re-set thus establishing a new leading edge for the pulse which is delayed by the pre-determined amount. The leading edge of this pulse is then fed into the set/reset flipflop composed of NAND gates NAG3 and NAG4 which is immediately set on this leading edge and re-set at a pre-determined time to establish the length of the pulse according to the desired duty cycle adjustment. This length adjustment is carried out by counters CTR10 and CTR11 which are pre-settable counters and which are fed at their pre-set data inputs by decade switches SW4. The counters CTR10 and CTR11 are immediately pre-set upon the receipt of the trailing edge of the pulse from the delay section and these counters count from the pre-set value at the clock rate selected by a mode select switch MS3 which is the same for the delay section. The pre-set count in counters CTR10 and CTR11 correspond to the percentage of the duty cycle which is desired that the output pulse consist of. Upon the generation of a carry-out output from counter CTR11, the set/re-set flipflop comprising gates NAG3 and NAG4 is re-set thus establishing the trailing edge of the jet pulse (JET 1 or JET 2) which is fed to the appropriate circuitry shown. The circuitry for creating the alarm comprises the exclusive NOR gate 13 which is fed by the output of the inverter 6 and which has as its other input the signal processed output of a pressure transducer 24 which measures the actual jet ventilation pulse of gas in the airway. As long as the two pulses fed to exclusive NOR gate 13 arrive at the same time, the output of the exclusive NOR gate will be zero thus establishing no output for amplifier A3. The signal from the pressure transducer 24 is converted to a digital value in amplifier circuit A4.

The frequency multiplier 17 comprises the circuitry including flipflops FF3-FF6 and NOR gate NOG4. This circuitry is connected to the output of the phase locked loop 2 in order to create the 5 KHz, 10 KHz, and 20 KHz signals necessary for operating the interval timer 18 when the circuitry is in the synchronous mode.

The mode select circuitry is shown in simplified form in FIG. 5 where a mode switch is externally available to the operator to decide whether the circuitry should operate in the synchronous or asynchronous mode. To the output of the mode switch is or-ed the signal MSEL which is the override signal created by the circuitry in FIG. 4 when no pulse is detected in the synchronous mode.

FIG. 7 shows the synchronization system of FIG. 2 with the addition of the propagation delay means 40 added therein for carrying out a digitally programmable propagation delay to compensate for the delays caused by the physical properties of the solenoid valve, the interconnecting tubing and the patient's anatomy. FIG. 8 shows the circuitry for the propagation delay compensation means according to the invention. As shown therein, the QRSS signal is fed into a flip-flop formed by NAND gates 41 and 42. The QRSS signal sets the flip-flop and the flip-flop is reset by a millisecond interval timer formed by counters 45 and 46 which are clocked at a one kilohertz rate at their clock inputs and which are digitally programmable to produce the output pulse at the carryout output of counter 45 so at to reset the flipflop at gate 42. The digital programming is carried out by switches SW 5 which programs in the units and tens place of the millisecond timer so that that the carry-out signal will occur at anywhere from 1 to 99 milliseconds in a manner similar to that of the previously described switches. The QRSS signal is also fed to inverter 43 which is connected to the preset enable input thus presetting the counters 45 and 46 to the programmed value upon receipt of the QRSS pulse. The counters then count down from that preset value which is a multiple of one millisecond for each count whereupon the carry out output of counter 45 resets the flip-flop by applying the pulse to gate 42 and the output TPD as shown in FIG. 9 goes to a logic 1 state. This enables the RPPM pulses at the input of AND 44 to be fed to the output thereof to form signal GC as shown in FIG. 9. Signal GC feeds count-up counters 47, 48 which are connected in series and which have their Q outputs connected to the inputs of latches 49 and 50 whose data outputs are connected to the series connected downcounters 51, 52. As a result of the circuitry 47-52, the output pulse TP is produced which, as shown in FIG. 9, represents the QRSS pulse which precedes the start of the next cardiac cycle by an amount equal to the programmed delay set on switch SW 5.

The flip-flop formed from NAND gates 53, 54 receives the output pulse TP at one input and the QRSS pulse at the other input thus producing at its output pulse PD which, as shown in FIG. 9, has a falling edge for triggering the delay second which occurs the number of millisecond equal to the width of pulse TPD earlier than the next QRSS signal and thus effectively compensates for propagation delays introduced by the interconnecting tubing, etc.

In use, the operator dials in the value of the transport delay in milliseconds. This value is derived from the type of valve used, length of interconnecting tubing, and anatomical considerations of the patent. Typically, the valve opening time is approximately 8 milliseconds, there is a twenty-five millisecond delay for a four foot interconnecting tube and a ten millisecond delay for transport of the pressure pulse down the trachea of a six foot tall, one hundred eighty pound male adult. This would yield a total transport delay of forty-three milliseconds.

Using the already available hundred pulses per QRS (RPPM) the number of pulses contained in the heart rate interval minus the propagation delay is determined. By delaying the onset of jet pulse by the aforementioned number of one millisecond pulses, the jet pulse will start the desired number of milliseconds earlier than the percent delay control otherwise indicates. In this way, the pressure pulse will always appear with the same percentage of delay, reference to the patient's R wave, despite varying heart rates. The attached FIG. 10 shows the relative timing relationship for the ECG, the jet drive pulse and the actual thoracic pressure pulse, wherein the transport delay is shown for at a heart rate of approximately one hundred fifty beats per minute.

It will be appreciated that the instant specification and claims are set forth by way of illustration and not limitation, and that various modifications and changes may be made without departing from the spirit and scope of the present invention.

What is claimed is:

1. A control system for a jet ventilator having means for controllably providing jet ventilation gas pulses to a patient, the control system comprising:
   means for producing periodic pulses;
   pulse-duration means for adjusting duration of the periodic pulses within the period thereof;
   pulse-delay means for adjusting delay of the periodic pulses within and proportionally to the period thereof; and
   control means responsive to the duration and delay adjusted pulses for correspondingly controlling the means for controllably providing the jet ventilation gas pulses to the patient.

2. The system according to claim 1, wherein the means for producing the periodic pulses comprises means for producing the pulses in synchronism with the patient's heart pulse rate comprising means receptive of an EKG signal from the patient for detecting the QRS component thereof and means responsive to the detected QRS component for producing the periodic pulses with a frequency proportional to the frequency of the detected QRS component.

3. The system according to claim 2, wherein the means for detecting the QRS component comprises a delta modulator receiving the EKG signal and having a slope overload condition defined by the step size and sampling rate thereof such that it goes into the slope overload condition only in response to the QRS component of the EKG signal for detecting the same.

4. The system according to claim 1, wherein the pulse-delay means comprises means for producing a predetermined number of equally spaced pulses during each period between successive ones of the periodic pulses and means responsive to a selected number thereof for adjusting the delay.

5. The system according to claim 1, wherein the means for producing the periodic pulses comprises means for producing the pulses asynchronously with respect to the patient's heart pulse rate and synchronously with respect to the patient's heart pulse rate; and further comprising mode selecting means for selecting one of the asynchronous and synchronous pulses as the periodic pulses.

6. The system according to claim 5, and further comprising means responsive to the absence of the patient's heart pulse rate over a peselected time when in the synchronous mode for changing the system to the asynchronous mode.

7. The system according to claim 5, and further comprising means for sensing the jet ventilation gas pulses and for producing a first pulse signal corresponding thereto and means for digitally comparing the first pulse signal with the duration adjusted and delayed periodic pulses for producing an alarm signal in response to an unfavorable comparison.

8. The control system according to claim 1, wherein the means for producing the periodic pulses comprises means responsive to an AC power line frequency for producing frequency-proportional pulses and a phase locked loop with a programmable counter in a feedback loop thereof for programmably frequency multiplying the pulses.

9. The control system according to claim 1, and additionally comprising means multiplying the frequency of the periodic pulses for the pulse delay means.

10. The control system according to claim 8 or 9, wherein the pulse-duration and pulse delay means each comprise a programmable counter selecting a number of the frequency-multiplied pulses for respectively adjusting the duration and delay of the periodic pulses.

* * * * *